(12) United States Patent
Liu

(10) Patent No.: US 7,152,458 B2
(45) Date of Patent: Dec. 26, 2006

(54) NANO-CRYSTALLINE AND/OR METASTABLE METAL HYDRIDES AS HYDROGEN SOURCE FOR SENSOR CALIBRATION AND SELF-TESTING

(75) Inventor: James Z. Liu, Rockford, IL (US)

(73) Assignee: Honeywell International Inc., Morristown, NJ (US)

( * ) Notice: Subject to any disclaimer, the term of this patent is extended or adjusted under 35 U.S.C. 154(b) by 138 days.

(21) Appl. No.: 11/001,410

(22) Filed: Nov. 30, 2004

(65) Prior Publication Data

US 2006/0117831 A1    Jun. 8, 2006

(51) Int. Cl.
G01N 7/00    (2006.01)

(52) U.S. Cl. ..................................... 73/23.2
(58) Field of Classification Search ............... 73/23.2
See application file for complete search history.

(56) References Cited

U.S. PATENT DOCUMENTS

| | | | |
|---|---|---|---|
| 4,522,190 A | 6/1985 | Kuhn et al. ................. 126/263 |
| 4,670,405 A * | 6/1987 | Stetter et al. ................ 436/151 |
| 5,033,284 A * | 7/1991 | Belt et al. ..................... 73/1.06 |
| 6,006,582 A * | 12/1999 | Bhandari et al. ............. 73/23.2 |
| 6,265,222 B1 * | 7/2001 | DiMeo, Jr. et al. ......... 436/144 |
| 6,387,152 B1 | 5/2002 | Klassen et al. |
| 6,450,007 B1 * | 9/2002 | O'Connor .................... 73/23.2 |
| 6,528,441 B1 | 3/2003 | Heung et al. |
| 6,539,774 B1 | 4/2003 | Zinck et al. ................. 73/23.2 |
| 6,564,633 B1 * | 5/2003 | Stormbom ............... 73/335.05 |
| 6,596,236 B1 * | 7/2003 | DiMeo, Jr. et al. ........... 422/88 |
| 6,742,650 B1 | 6/2004 | Yang et al. .................. 206/0.7 |
| 2001/0003249 A1 * | 6/2001 | Stormborn ................... 73/1.06 |
| 2002/0100682 A1 | 8/2002 | Kelley et al. ................. 204/266 |
| 2003/0037590 A1 * | 2/2003 | Stark ............................ 73/1.03 |
| 2003/0207156 A1 | 11/2003 | Ovshinsky et al. ............ 429/9 |
| 2004/0075140 A1 * | 4/2004 | Baltes et al. ................. 257/347 |
| 2004/0142203 A1 | 7/2004 | Woolley ...................... 428/615 |
| 2004/0166057 A1 | 8/2004 | Schell et al. ............. 423/658.2 |

FOREIGN PATENT DOCUMENTS

| | | |
|---|---|---|
| JP | 60205246 | 10/1985 |
| WO | WO 99/17110 | 4/1999 |
| WO | WO 2005/119248 | 12/2005 |

OTHER PUBLICATIONS

R. Schulz, et al., "Hyddrogen Sorption In Mechanically Alloyed Nanocrystalline and Disordered Materials", Proceedings of the 22nd Rise International Symposium on Materials Science: Science of Metastable and Nanocrystalline Alloys Structure, Properties and Modeling, Denmark 2001: pp. 141-153.

A. Peter Jardine, "Hydrogen Sensors for Hydrogen Fuel Cell Applications", DCH Technology Inc., Valencia, CA, Copyright 2000, Darnell Group, Inc.; pp. 1-7.

* cited by examiner

*Primary Examiner*—Hezron Williams
*Assistant Examiner*—Rodney T. Frank
(74) *Attorney, Agent, or Firm*—Kermit D. Lopez; Luis M. Ortiz

(57) ABSTRACT

Sensor systems and methods are disclosed herein. In general, a sensor can be provided for detecting the presence of a gas (e.g., hydrogen) in an area proximate to the sensor component. A composite material is generally associated with the sensor, wherein the composite material comprises a metal hydride material for gas storage. A heater can also be provided that heats the metal hydride material to a particular temperature at which hydrogen is released from the metal hydride material in order to calibrate and self-test the sensor for detecting the presence of gas.

21 Claims, 3 Drawing Sheets

NANO-CRYSTALLINE AND/OR METASTABLE METAL HYDRIDES AS HYDROGEN SOURCE FOR SENSOR CALIBRATION AND SELF-TESTING

TECHNICAL FIELD

Embodiments are generally related to sensor methods and systems. Embodiments are also related to methods and systems for calibrating sensors. Embodiments are additionally related to nano-crystalline and meta-stable metal hydride materials adapted for use with sensor devices and systems thereof.

BACKGROUND OF THE INVENTION

Gas sensors, such as hydrogen sensors, are utilized in a number of commercial, consumer and industrial applications. Hydrogen, for example, is a flammable and explosive gas with a wide variety of industrial and scientific uses. Well-known industrial uses of hydrogen include the production of basic staple products of chemical industry such as ammonia and fertilizers derived therefrom, basic alcohols, hydrogen chloride, reduction of ores for manufacturing of metals, refinery of oil for manufacturing of petroleum, hydrogenation of vegetable oils for margarine and related industries, and many other uses.

Hydrogen is also widely used for space flight applications, for instance as a component of hydrogen-oxygen blends used in vehicular propulsion systems. Hydrogen is also used in a variety of metal forming and microelectronic processing steps which are often of extreme importance in device fabrication and metal interconnect processing of multi-level devices.

There has been also an increasing emphasis on the use of fuel cells, which require hydrogen as a fuel in various stationary and mobile applications, for instance, in fuel cells of automobiles.

It is axiomatic that handling hydrogen requires utilization of robust safety devices as it is a highly flammable gas at a concentration in air as low as 4% by volume. The ability to detect stray emissions of hydrogen is, therefore, mandatory, and is an important feature of any process or device where hydrogen is used.

In these and other applications, hydrogen sensors are employed to monitor the environment around which hydrogen is utilized, to ensure the efficiency, safety and operational integrity of the system. For such purposes, a number of hydrogen sensors and complex detection methods have been developed and are in common use.

Calibration and self-testing of sensors, such as hydrogen sensing devices, is an important feature for both safety and efficiency purposes. One of the problems with conventional sensor calibration and/or self testing methods and systems is that in order to successfully operate such devices, various chemical compounds must be heated quickly, efficiently and safely.

BRIEF SUMMARY

The following summary is provided to facilitate an understanding of some of the innovative features unique to the embodiments disclosed herein and is not intended to be a full description. A full appreciation of the various aspects of the embodiments can be gained by taking the entire specification, claims, drawings, and abstract as a whole.

It is, therefore, one aspect of the present invention to provide for improved sensor devices, methods, and systems.

It is another aspect of the present invention to provide for improved calibration and self-testing methods and systems.

It is a further aspect of the present invention to provide for the use of metastable metal hydrides as a hydrogen source for gas (e.g., hydrogen) sensor calibration and self-testing.

It is an additional aspect of the present invention to provide for the use of nano-crystalline metal hydrides as a hydrogen source for gas (e.g., hydrogen) sensor calibration and self-testing.

The aforementioned aspects and other objectives and advantages can now be achieved as described herein. Sensor systems and methods are disclosed herein. In general, a sensor can be provided for detecting the presence of gas (e.g., hydrogen) in an area proximate to the sensor component. A composite material is generally associated with the sensor, wherein the composite material comprises a metal hydride material for gas (e.g., hydrogen) storage. A heater can also be provided that heats the metal hydride material to a particular temperature at which a gas is released from the metal hydride material in order to calibrate and self-test the sensor for detecting the presence of gas (e.g., hydrogen). Because of the cross-sensitivities among gas sensors, for certain target gases, test and calibration can be done using another gas, called a reference gas, to which a gas sensor is cross sensitive.

Table 1 below illustrates cross sensitivities as exemplified by certain gas sensors. Other sensors can exhibit different cross sensitivities. For each gas sensor, however, known cross sensitivities allow use of a reference gas to calibrate the sensor.

TABLE 1

Cross Sensitivity Effects for Certain Sensors

| sensor | Calibration Gas | Target Gas Equivalence |
|---|---|---|
| 0–10 ppm acid gas | 10 ppm chlorine | 10 ppm acid gas |
| 0–10 ppm nitrogen dioxide | 10 ppm chlorine | 9 ppm nitrogen dioxide |
| 0–25 ppm hydrogen cyanide | 10 ppm sulphur dioxide | 28 ppm hydrogen cyanide |
| 0–10 ppm chlorine dioxide | 10 ppm chlorine | 4 ppm chlorine dioxide |
| 0–2.5 ppm phosphine | 10 ppm sulphur dioxide | 2 ppm phosphine |
| 0–1 ppm ozone | 2 ppm chlorine | 1 ppm ozone |
| 0–10 ppm hydrogen fluoride | 5 ppm hydrogen chloride | 10 ppm hydrogen fluoride |

The metal hydride material can be configured as a metastable metal hydride material, which may be utilized in the form of a powder. The metastable metal hydride material is dispersed throughout a porous matrix of polymeric material, such as, for example, polyethylene. The metal hydride material can also be implemented as an amorphous structure comprising a nano-crystalline material. The nano-crystalline material is structurally characterized by a plurality of ultra-fine grains separated by a large number of grain boundaries thereof.

The metal hydride material is heated to a first temperature for a first time period to attain equilibrium thereof in order to release a first known amount of the hydrogen in order for the sensor to react with the hydrogen and thereafter compare a response thereof to a stored number in order to determine if a modification to the sensor is required for calibration thereof. The metal hydride material can then be heated to a second temperature for a second time period thereof in order to release a second known amount of the hydrogen in order for the sensor to react with the hydrogen and thereafter compare a response thereof to the stored number in order to determine if a modification to the sensor is required for calibration thereof. The metal hydride material may also be heated to a third temperature for a third time period thereof in order to release a third known amount of the hydrogen in order for the sensor to react with the hydrogen and thereafter compare a response thereof to the stored number in order to determine if a modification to the sensor is required.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope of the claims disclosed herein.

Figure 1:
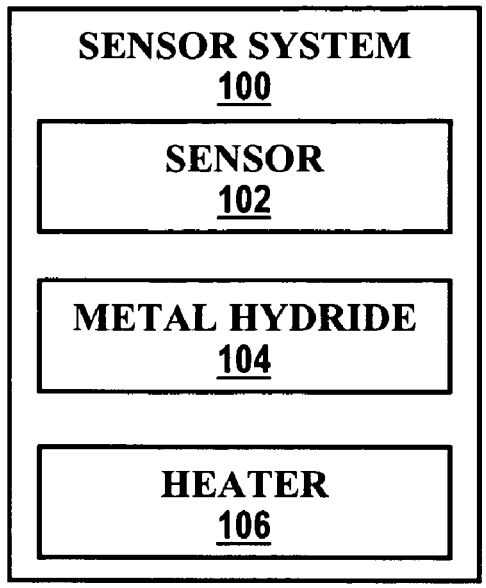
FIG. 1 illustrates a high-level block diagram of a system, which can be implemented in accordance with a preferred embodiment.

FIG. 1 illustrates a high-level block diagram of a system 100, which can be implemented in accordance with a preferred embodiment. System 100 generally includes a sensor 102 for detecting the presence of gas in an area proximate to said sensor component. A composite material 104 is generally associated and/or incorporated into sensor 102. In the configuration of system 100 composite material 104 comprises a metal hydride material for hydrogen storage. System 100 also includes a heater 106 for heating said metal hydride material to a particular temperature at which hydrogen is released from said metal hydride material in order to calibrate and self-test said sensor 102 for detecting the presence of gas.

Heater 106 can be implemented as any of a number of heating devices. For example, heater 106 can be configured as a flexible heater material heat pad composed of a composite material. An example of such a heater is disclosed in U.S. Pat. No. 4,522,190, "Flexible Electromechanical Heater," which issued to Kuhn et al on Nov. 3, 1983, and is incorporated herein by reference. Note that the flexible heater of Kuhn et al is disclosed for general edification and illustrative purposes only and is not considered a limiting feature of the embodiments disclosed herein. It is understood that other types of heaters can be utilized to implement heater 106.

Figure 2:
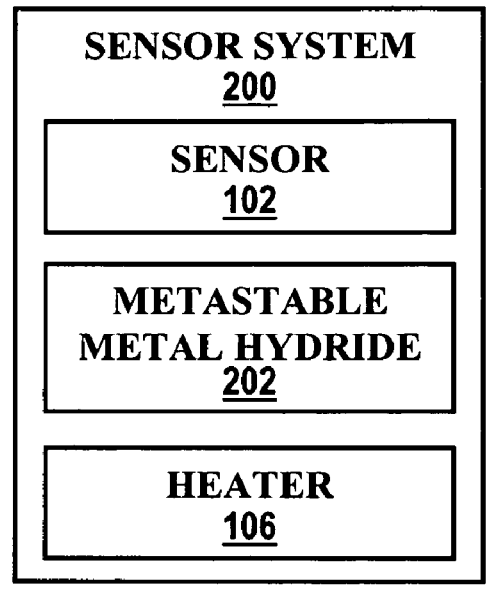
FIG. 2 illustrates a high-level block diagram of a system, which can be implemented in accordance with an alternative embodiment.

FIG. 2 illustrates a high-level block diagram of a system 200, which can be implemented in accordance with an alternative embodiment. Note that in FIGS. 1–3, identical or similar parts are generally indicated by identical reference numerals. Thus, system 200 generally includes a sensor 102 for detecting the presence of gas (e.g., hydrogen) in an area proximate to said sensor component. The composite material 202 is generally associated and/or incorporated into sensor 102. In the configuration of system 200 composite material 104 comprises a metastable metal hydride material for hydrogen storage. System 200 also includes heater 106 for heating said metal hydride material to a particular temperature at which hydrogen is released from said metal hydride material in order to calibrate and self-test said sensor 102 for detecting the presence of gas (e.g., hydrogen).

Figure 3:
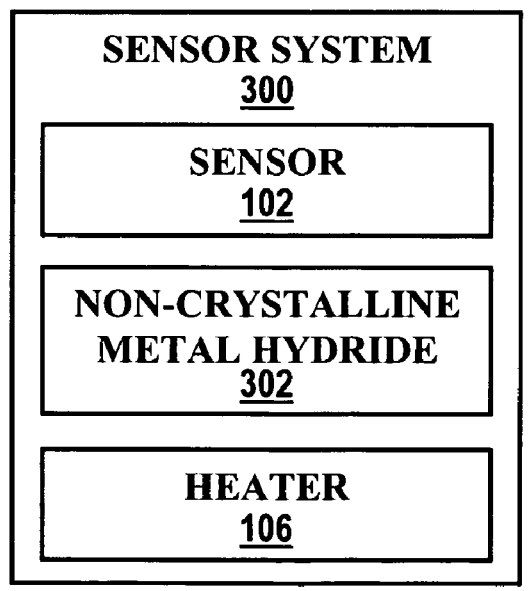
FIG. 3 illustrates a high-level block diagram of a system, which can be implemented in accordance with an alternative embodiment.

FIG. 3 illustrates a high-level block diagram of a system 300, which can be implemented in accordance with an alternative embodiment. System 300 generally includes a sensor 102 for detecting the presence of gas (e.g., hydrogen) in an area proximate to said sensor component. The composite material 104 is generally associated and/or incorporated into sensor 102. In the configuration of system 300, the composite material 302 comprises a nano-crystalline metal hydride material for hydrogen storage. System 300 also includes heater 106 for heating said metal hydride material to a particular temperature at which hydrogen is released from said metal hydride material in order to calibrate and self-test said sensor 102 for detecting the presence of a gas (e.g., hydrogen).

The nano-crystalline metal hydride material of composite material 302 can be configured as an amorphous structure that it obtained after milling/grinding. Data associated with such material 302 is illustrated in further detail herein with respect to FIGS. 5–6. Mechanical alloying can be utilized to produce the nano-crystalline material. Mechanical grinding can also be utilized in the production such nano-crystalline material.

Figure 4:
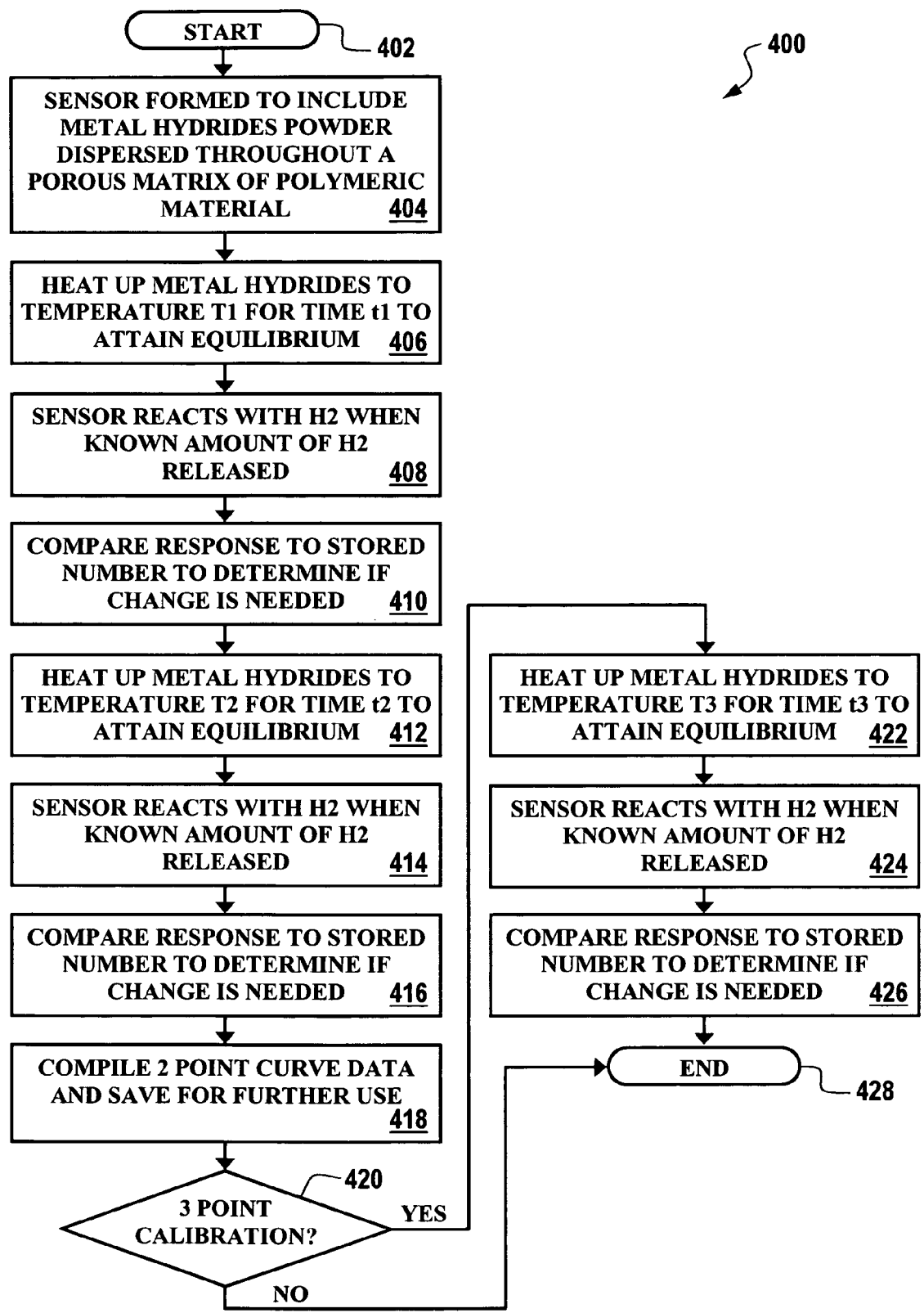
FIG. 4 illustrates a high-level flow chart of operations illustrating logical operational steps that can be implemented in accordance with one embodiment.

FIG. 4 illustrates a high-level flow chart 400 of operations illustrating logical operational steps that can be implemented in accordance with one embodiment. As indicated above, metal hydride material can be utilized for hydrogen (H2) storage. Thus, as indicated at block 402, the process can be initiated. Next, as indicated at block 404, a sensor can be formed to include or be associated with metal hydride powder dispersed throughout a porous matric of polymeric material, such as, for example, polyethylene.

As indicated thereafter at block 406, the metal hydrides (i.e., metastable metal hydrides and/or nanocrystalline metal hydrides) can be heated utilizing a heater such as heater 106 of FIGS. 1–3 to a temperature T1 for a time t1 (i.e., to attain equilibrium). As indicated next at block 408, a known amount of H2 can then be released, and the sensor or sensors (e.g., sensor 102 of FIGS. 1–3) can react with the H2. Thereafter, as illustrated at block 410, the response can be compared to a stored number or value to determine if additionally changes are required for calibration purposes of, for example, systems 100–300 depicted in FIGS. 1–3.

The metal hydrides can then be heated to a temperature T2 for a time t2 (i.e., to attain equilibrium) as depicted at block 412 and a second known amount of H2 can be released, such that the sensor or sensors react with H2, as indicated thereafter at block 414. As depicted next at block 416, the response can be compared to the stored number or value to determine if changes are required for sensor calibration purposes. Next, the sensor or system 100, 200 or 300 can utilize the foregoing 2 point evaluation to fit a curve, and save such data thereof for additional uses.

As indicated next at block 420, a test can be performed to determine if an additional calibration is necessary. If so, then the operates depicted at blocks 422, 424 and 426 are performed. If not, the process ends, as indicated at block 428. Note that in some embodiments, a self-test can be accomplished with less heating time and does not need to reach equilibrium. For example, a 5 second heat up time may be required, and the amount of H2 generated may vary. In some embodiments, the self-test can be performed weekly, while self-calibration can be performed twice a year.

Figure 5:
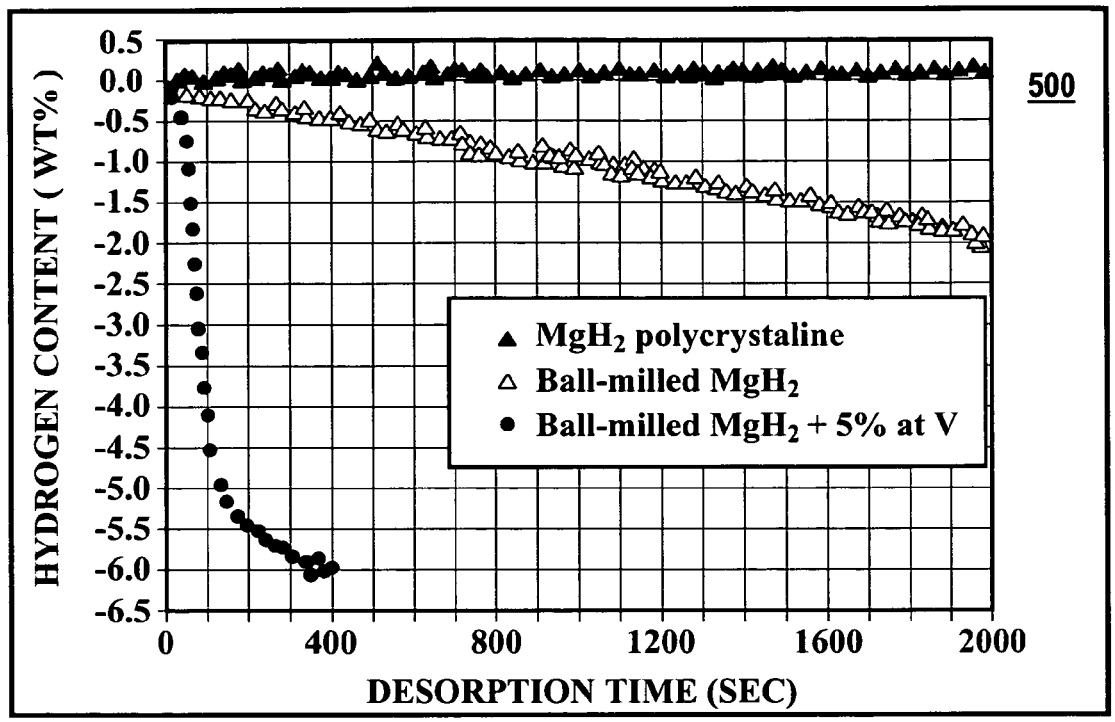
FIG. 5 illustrates a graph of hydrogen content versus desorption time indicative of data, which may be generated in accordance with one embodiment.
Figure 6:
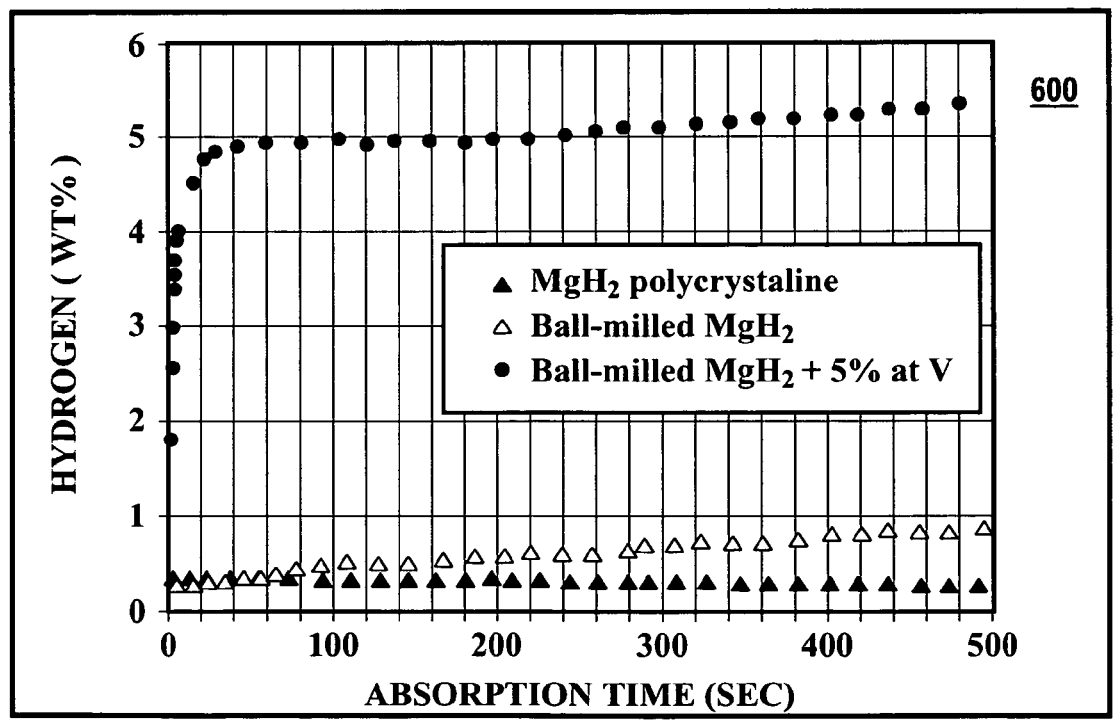
FIG. 6 illustrates a graph of hydrogen content versus desorption time indicative of data, which may be generated in accordance with another embodiment.

FIG. 5 illustrates a graph 500 of hydrogen content versus desorption time indicative of data, which may be generated in accordance with one embodiment. FIG. 6 illustrates a graph 600 of hydrogen content versus desorption time indicative of data, which may be generated in accordance with another embodiment. As indicated above, nano-crystalline metal hydride material (e.g., composite material 302 of FIG. 3) or an amorphous structure thereof can be obtained after milling and/or grinding. The activation and the kinetics of absorption and desorption are improved primarily in low temperature metal hydride systems.

The loss of storage capacity is not a concern for a self test self-calibration sensor device such as system 300 of FIG. 3. The significantly reduced desorption time, as indicated by the data depicted in graph 500 of FIG. 5, however, is a great advantage for a self test and/or self-calibration sensor system such as system 300 of FIG. 3. Nano-crystalline materials are structurally characterized by ultra-fine grains (e.g., <100 nm) separated by a large number of grain boundaries. Properties of nano-crystalline hydrides often differ significantly from those counterparts with large grains. Milled powders therefore require no or much milder activation in order to absorb or desorb hydrogen. The sorption kinetic is also usually much better. As the grain size becomes smaller and smaller, the ratio of the grain boundary to crystalline phases increases.

It is important to note that although embodiments disclosed herein have discussed hydrogen sensor applications, such embodiments can be adapted for detecting other types of gas, such as those listed in Table 1 herein. Thus, the embodiments discussed herein can be utilized to calibrate not only hydrogen sensors, but any number of a variety of gas sensor types.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A sensor system, comprising:
a sensor for detecting the presence of a gas in an area proximate to said sensor component;
a composite material associated with said sensor, wherein said composite material comprises a metal hydride material comprising a nano-crystalline material for storage of gas, wherein said nano-crystalline material is structurally characterized by a plurality of ultra-fine grains separated by a large number of grain boundaries thereof; and
a heater for heating said metal hydride material to a particular temperature at which a gas is released from said metal hydride material in order to calibrate and self-test said sensor for detecting the presence of said gas.

2. The system of claim 1 wherein said gas comprises hydrogen.

3. The system of claim 1 wherein said metal hydride material comprises a metastable metal hydride material.

4. The system of claim 3 wherein said metastable metal hydride material comprises a powder.

5. The system of claim 3 wherein said metastable metal hydride material is dispersed throughout a porous matrix of polymeric material.

6. The system of claim 5 wherein said polymeric material comprises polyethylene.

7. The system of claim 3 wherein said metal hydride material is heated to a first temperature for a first time period to attain equilibrium thereof in order to release a first known amount of said hydrogen in order for said sensor to react with said hydrogen and thereafter compare a response thereof to a stored number in order to determine if a modification to said sensor is required for calibration thereof.

8. The system of claim 7 wherein said metal hydride material is heated to a second temperature for a second time period thereof in order to release a second known amount of said hydrogen in order for said sensor to read with said hydrogen and thereafter compare a response thereof to said stored number in order to determine if a modification to said sensor is required for calibration thereof.

9. The system of claim 8 wherein said metal hydride material is heated to a third temperature for a third time period thereof in order to release a third known amount of said hydrogen in order for said sensor to react with said hydrogen and thereafter compare a response thereof to said stored number in order to determine if a modification to said sensor is required.

10. The system of claim 1 wherein said metal hydride material comprises an amorphous structure.

11. A sensor system, comprising:
a sensor for detecting the presence of hydrogen in an area proximate to said sensor component;
a composite material associated with said sensor, wherein said composite material comprises a metal hydride material for hydrogen storage, wherein said metal hydride material comprises a nano-crystalline material; and
a heater for heating said metal hydride material to a particular temperature at which hydrogen is released from said metal hydride material in order to calibrate and self-test said sensor for detecting the presence of hydrogen.

12. A sensor method, comprising:
providing a sensor for detecting the presence of a gas in an area proximate to said sensor component, wherein said gas comprises hydrogen;
associating a composite material associated with said sensor, wherein said composite material comprises a metal hydride material for gas storage;
configuring said metal hydride material to comprise a metastable metal hydride material; and
heating said metal hydride material utilizing a heater to a particular temperature at which gas is released from said metal hydride material in order to calibrate and self-test said sensor for detecting the presence of said gas.

13. The method of claim 12 further comprising the step of providing said metastable metal hydride material as a powder thereof.

14. The method of claim 10 wherein said metastable metal hydride material is dispersed throughout a porous matrix of polymeric material.

15. The method of claim 14 wherein said polymeric material comprises polyethylene.

16. The method of claim 12 further comprising the step of:
heating said metal hydride material to a first temperature utilizing said heater for a first time period to attain equilibrium thereof in order to release a first known amount of said hydrogen in order for said sensor to react with said hydrogen; and
thereafter comparing a response thereof to a stored number in order to determine if a modification to said sensor is required for calibration thereof.

17. The method of 16 further comprising the steps of:
thereafter heating said metal hydride material utilizing said heater to a second temperature for a second time period thereof in order to release a second known amount of said hydrogen in order for said sensor to react with said hydrogen; and
thereafter comparing a response thereof to said stored number in order to determine if a modification to said sensor is required for calibration thereof.

18. The method of claim 16 further comprising the step of:
thereafter heating said metal hydride material utilizing said heater to a third temperature for a third time period thereof in order to release a third known amount of said hydrogen in order for said sensor to react with said hydrogen; and
thereafter comparing a response thereof to said stored number in order to determine if a modification to said sensor is required.

19. The method of claim 10 further comprising the step of configuring said metal hydride material to comprise an amorphous structure.

20. The method of claim 19 wherein said metal hydride material comprises a nano-crystalline material.

21. The method of claim 20 wherein said nano-crystalline material is structurally characterized by a plurality of ultra-fine grains separated by a large number of grain boundaries thereof.

* * * * *

UNITED STATES PATENT AND TRADEMARK OFFICE
CERTIFICATE OF CORRECTION

PATENT NO. : 7,152,458 B2 Page 1 of 1
APPLICATION NO. : 11/001410
DATED : December 26, 2006
INVENTOR(S) : James Z. Liu It is certified that error appears in the above-identified patent and that said Letters Patent is hereby corrected as shown below:

In Column 6, line 28, delete "read" and add --react--

Signed and Sealed this

Fourth Day of March, 2008

JON W. DUDAS
*Director of the United States Patent and Trademark Office*